US012677829B2

(12) United States Patent
Becker et al.

(10) Patent No.: US 12,677,829 B2
(45) Date of Patent: *Jul. 14, 2026

(54) STABLE MICROBIAL COMPOSITION AND DRYING PROCESS

(71) Applicant: DANISCO US INC, Palo Alto, CA (US)

(72) Inventors: Nathaniel T. Becker, Palo Alto, CA (US); Amruta Bedekar, Palo Alto, CA (US); Regina Arakel Hermansen, Palo Alto, CA (US); Katherine Hoffmann, Palo Alto, CA (US); Amanda Kathleen Iverson, Palo Alto, CA (US); Samuel A. Maurer, Palo Alto, CA (US); Aleksandra Virag, Palo Alto, CA (US)

(73) Assignee: DANISCO US INC., Palo Alto, CA (US)

( * ) Notice: Subject to any disclaimer, the term of this patent is extended or adjusted under 35 U.S.C. 154(b) by 1121 days.

This patent is subject to a terminal disclaimer.

(21) Appl. No.: 17/288,616

(22) PCT Filed: Oct. 24, 2019

(86) PCT No.: PCT/US2019/057823
§ 371 (c)(1),
(2) Date: Apr. 26, 2021

(87) PCT Pub. No.: WO2020/086821
PCT Pub. Date: Apr. 30, 2020

(65) Prior Publication Data
US 2021/0392880 A1 Dec. 23, 2021

Related U.S. Application Data

(60) Provisional application No. 62/751,169, filed on Oct. 26, 2018.

(51) Int. Cl.
| | |
|---|---|
| *A01N 25/12* | (2006.01) |
| *A01N 63/20* | (2020.01) |
| *A01N 63/22* | (2020.01) |
| *A01N 63/32* | (2020.01) |
| *A01N 63/38* | (2020.01) |
| *A23K 10/18* | (2016.01) |
| *A23K 10/30* | (2016.01) |
| *A23K 20/105* | (2016.01) |
| *A23K 20/163* | (2016.01) |
| *A23K 20/28* | (2016.01) |
| *A23L 33/125* | (2016.01) |
| *A23L 33/135* | (2016.01) |
| *A23L 33/14* | (2016.01) |

(Continued)

(52) U.S. Cl.
CPC ............. *A01N 25/12* (2013.01); *A01N 63/20* (2020.01); *A01N 63/22* (2020.01); *A01N 63/32* (2020.01); *A01N 63/38* (2020.01); *A23K 10/18* (2016.05); *A23K 10/30* (2016.05); *A23K 20/105* (2016.05); *A23K 20/163* (2016.05); *A23K 20/28* (2016.05); *A23L 33/125* (2016.08); *A23L 33/135* (2016.08); *A23L 33/14* (2016.08); *A23L 33/16* (2016.08); *A61K 9/1611* (2013.01); *A61K 9/1623* (2013.01); *A61K 9/1635* (2013.01); *A61K 35/741* (2013.01); *A61K 35/742* (2013.01); *A61K 36/062* (2013.01); *A61K 36/064* (2013.01); *A23V 2002/00* (2013.01); *A61K 2035/115* (2013.01)

(58) Field of Classification Search
CPC ........ A01N 25/12; A01N 63/20; A23K 10/18; A23K 10/30; A23K 20/105; A23K 20/163; A23K 20/28; A23L 33/125; A23L 33/135; A23L 33/14; A23L 33/16; A61K 9/1611
See application file for complete search history.

(56) References Cited

U.S. PATENT DOCUMENTS

| | | | |
|---|---|---|---|
| 5,929,507 A | 7/1999 | Gonzalez et al. | |
| 7,713,725 B2 | 5/2010 | England et al. | |

(Continued)

FOREIGN PATENT DOCUMENTS

| | | | | |
|---|---|---|---|---|
| CA | 2820178 A1 * | 6/2012 | ............ | A21D 8/045 |
| WO | 9602638 A1 | 2/1996 | | |

(Continued)

OTHER PUBLICATIONS

Food and Drug Administration FDA (Talc, https://www.fda.gov/cosmetics/cosmetic-ingredients/talc#:~:text=Talc%20is%20a%20naturally%20occurring,and%20other%20personal%20care%20products, Dec. 7, 2022) (Year: 2022).*

(Continued)

*Primary Examiner* — Louise W Humphrey
*Assistant Examiner* — Alexander M Duryee

(57) ABSTRACT

The present invention relates to a microbial composition having fermentation solids embedded in a matrix forming an evaporated suspension, characterized by the features of having: a non-hygroscopic matrix and fermentation solids at a ratio of at least 1:1 by weight; wherein the matrix has a moisture-regulating binder and a detackifier at a ratio of between 1:5 and 5:1 by weight and, optionally, not more than 75% by weight protective stabilizer; wherein the evaporated suspension has a water content of at least 1% and at most 30% water by weight when stored at a relative humidity of 50% and a temperature of 20° C. The present invention also relates to granules and methods for preparing a composition having fermentation solids embedded in a matrix to form an evaporated suspension.

30 Claims, 1 Drawing Sheet

(51) Int. Cl.

| | | |
|---|---|---|
| *A23L 33/16* | (2016.01) | |
| *A61K 9/16* | (2006.01) | |
| *A61K 35/00* | (2006.01) | |
| *A61K 35/741* | (2015.01) | |
| *A61K 35/742* | (2015.01) | |
| *A61K 36/062* | (2006.01) | |
| *A61K 36/064* | (2006.01) | |

(56) References Cited

U.S. PATENT DOCUMENTS

| | | | |
|---|---|---|---|
| 9,308,271 | B2 | 4/2016 | Yde |
| 9,469,835 | B2 | 10/2016 | Bronshtein |
| 2009/0074809 | A1 | 3/2009 | Jackson et al. |
| 2012/0014253 | A1 | 1/2012 | Rongong et al. |
| 2014/0004083 | A1 | 1/2014 | Hollard et al. |

FOREIGN PATENT DOCUMENTS

| | | | | |
|---|---|---|---|---|
| WO | 2014063237 | A1 | 5/2014 | |
| WO | 2016113665 | A1 | 7/2016 | |
| WO | WO-2016113666 | A1 * | 7/2016 | ............. A01N 25/26 |
| WO | 2017143130 | A1 | 8/2017 | |

OTHER PUBLICATIONS

International Search Report and Written Opinion from PCT Application No. PCT/EUS2019/057823 dated Jan. 17, 2020, 8 pages.

* cited by examiner

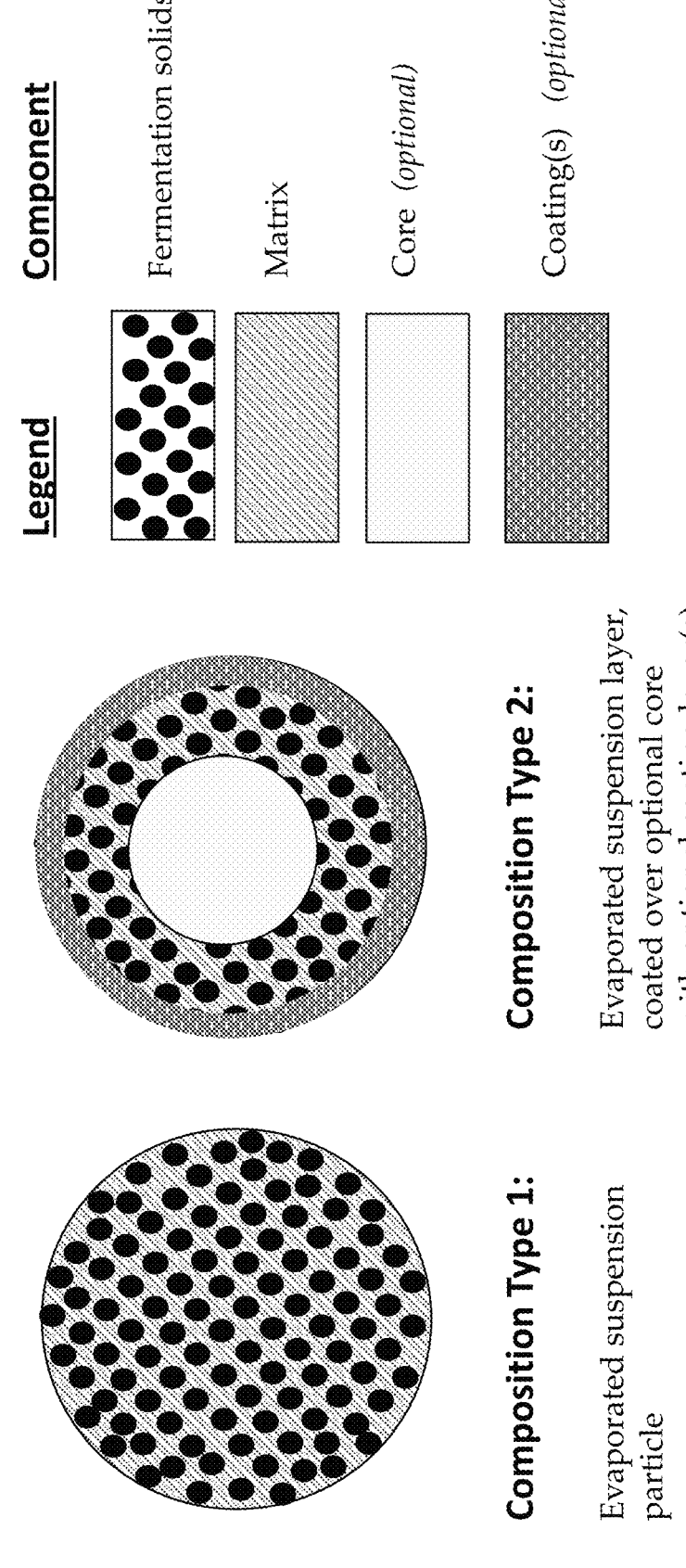

STABLE MICROBIAL COMPOSITION AND DRYING PROCESS

TECHNICAL FIELD

The present compositions and methods relate to formulations and process conditions for stabilizing microorganisms for extended storage under ambient conditions without refrigeration, humidity control, or special packaging.

BACKGROUND

Microorganisms such as bacteria, fungi and yeast can provide benefits to animals and plants by stimulating growth, by enhancing nutrition and immunity, and by controlling diseases and damage from pests. When found in close association with the host animal or plant, these microorganisms provide such essential or beneficial services to the host. In recent years, there has been considerable commercial interest in exogenously supplying such beneficial microorganisms, often called probiotics or biologicals, to provide their beneficial functions more consistently or beyond what is typically present endogenously, or even to alter the microbiome balance to inhibit or exclude colonization by microorganisms which are pathogenic or otherwise detrimental to the host organism.

Delivery of beneficial microorganisms in product form to plants and animals requires not only assurance of their biological efficacy, but also maintenance of their viability and efficacy during manufacture, storage and use. Certain microbial structures of microorganisms are inherently stable, such as robust vegetative cells, or spores. U.S. Pat. No. 5,929,507 describes a composition suitable for stabilizing microorganisms for use as plant seed inoculants, by combining the microorganisms with soluble non-crosslinked polysaccharides such as alginate. The utility of alginate encapsulation, though, is tempered and limited by the fact that the exemplified inoculant bacteria (e.g., *Rhizobia japonica* and *Serratia liquifaciens*) are thermally stable and survive quite well under ambient conditions without addition of special protective stabilizers.

However, many beneficial microorganisms are sensitive to temperature, moisture, and oxygen, and other environmental stressors, and hence tend to lose viability quickly, sometimes within hours or days. It is generally known that the shelf life of viable microorganisms can be ensured or improved by storage under refrigeration, in a dry format, at low water activity, or in packaging with controlled humidity and permeability. Water activity of the microorganisms can be reduced to low levels, e.g., below 0.4, 0.2 or even below 0.1, by drying processes such as lyophilization or freeze drying, generally in combination with addition of protective stabilizers. U.S. Pat. No. 9,469,835 describes a means of stabilizing a variety of microorganisms, including bacteria and fungi, by a vitrification process. The patent described a two-step drying process, first under vacuum from a partially-frozen slush state at near subzero temperatures, followed by drying at temperatures above 40° C. until a very low water content and low water activity is achieved. This process is asserted to produce a mechanically stable foam with significantly elevated glass transition temperature ($T_g$) such that the biological is at no time subjected to temperatures as high as the $T_g$.

U.S. Patent Pub. No. 2014/0004083 discloses a cryoprotectant system for preserving microorganisms such as lactic acid bacteria, by addition of a non-reducing sugar, such as trehalose, combined with inositol in a specified range of ratios, and thereafter freezing, vacuum drying, or freeze-drying the composition for dry storage. U.S. Pat. No. 9,308,271 describes a cryoprotectant system for preserving lactic acid bacteria, by addition of trehalose, inulin, and hydrolyzed casein, in the absence of alginate, thereafter freeze-drying the composition, and storing the composition at up to 35° C. and at a water activity of 0.3 or less. In such cases where a microbial composition has been freeze-dried or vacuum-dried, low water activity can be maintained by packaging the microbial composition within capsules, bottles, or pouches composed of barrier materials with low water vapor permeability.

Some attempts have been made to provide compositions that preserve the viability of microbes during storage at ambient temperature and humidity, without freeze drying or special packaging. U.S. Patent Pub. No. 2012/014253 describes a composition and process for stabilizing dehydrated microorganisms by producing a core particle comprising dried organisms and coating the core particle with hygroscopic salts, such as a mixture of phosphate salts. The hygroscopic salt coating in effect acts as a water decoy, attracting moisture from the environment and trapping it before it can diffuse into the dehydrated microorganisms in the core particle. While the examples provide some evidence of stability enhancement during storage at moderate humidity conditions, the hygroscopic salt layer eventually saturates with absorbed water, and ultimately loses its ability to protect moisture-sensitive microorganisms from taking up water and losing viability. Thus, there remains a need for a robust and sustained way to limit the continued uptake of water, and thereby preserve the viability of microorganisms stored at ambient temperature and humidity conditions, without the need for special packaging or other measures to refrigerate and maintain low water activity of the microorganisms.

While refrigeration, humidity control, and special packaging measures are suitable and economical in certain applications, e.g., human therapeutics, nutraceuticals, dietary supplements, or foods, there are several important industrial applications where it is not practical or economical to package or store the microbial products under controlled temperature and humidity conditions, or with special packaging with low permeability to water vapor.

For example, in agricultural crop applications, microbial products intended to stimulate plant growth or control plant pests and diseases are typically formulated either as liquids or as dry formulations stored without refrigeration or humidity resistant packaging, and applied in the open environment via seed coatings, foliar sprays, or in-furrow powders or granules. Liquid formulations for crop application include aqueous solutions or suspensions and non-aqueous formulations such as oils, emulsions, and suspo-emulsions. Dry formulations include wettable powders and granules that can be applied directly in the field or diluted to form sprayable solutions or suspensions that can be sprayed onto plants.

In feed animal health applications, microbial products intended to improve health or protect against disease are typically introduced into drinking water or mixed into dry animal feed mash composed of grains with significant free water content. The dry feed mash is often further formed into pellets by means of a steam pelleting process, wherein live steam is mixed with the feed and extruded through a die at temperatures of 80-100° C. The microbial products, either neat or in pelleted or unpelleted animal feed, must remain viable during storage in warehouses without refrigeration, humidity control or special packaging, for 3-12 months or longer.

For food and beverage applications, microorganisms are often incorporated to provide probiotic benefits. In moist foods such as snack bars, or beverages such as yogurt or fruit juice, the incorporated microorganisms must remain viable for several months or longer. Probiotic organisms are also incorporated into pet foods such as kibbles. In these applications, there is often no provision for refrigerated storage or special packaging to protect against humidity.

Microorganisms suitable as beneficial agents in the applications described above include any bacteria, yeast or fungi, and can comprise multiple different cell morphologies, including vegetative cells, mycelia, spores, or cysts. Depending on the particular species, certain of these forms may have significantly enhanced storage stability. For example, many bacterial and fungal species produce spores that retain viability during extended periods of dormancy, for months or even years, until re-activated under germination conditions.

However, many microbial structures do not remain viable under ambient conditions, i.e. temperatures above about 10° C., most typically 20-30° C., and humidity/above 10% RH, most typically 30-60% RH, for extended storage periods, i.e., longer than one day, most typically 3-52 weeks. For example, many vegetative bacterial cells, fungal spores, and fungal microsclerotia do not show extended viability at these conditions.

There is a need for shelf-stable microbial formulations and processes for producing such formulations, that ensure improved viability of the microorganisms during storage under ambient conditions, e.g., at conditions that do not require refrigeration, humidity control or special packaging.

SUMMARY

The present compositions and methods relate to excipients and process conditions for extending the storage life of microorganisms.

1. In one aspect, a microbial composition comprising fermentation solids embedded in a matrix forming an evaporated suspension is provided, characterized by the features of having: a non-hygroscopic matrix and fermentation solids at a ratio of at least 1:1 by weight; wherein the matrix comprises a moisture-regulating binder and a detackifier at a ratio of between 1:5 and 5:1 by weight and, optionally, not more than 75% by weight protective stabilizer; wherein the evaporated suspension has a water content of at least 1% and at most 30% water by weight when stored at a relative humidity of 50% and a temperature of 20° C.

2. In some embodiments of the composition of paragraph 1, the binder, detackifier, and optional protective stabilizer each have less than 10% water uptake at 50%, and optionally 75%, relative humidity.

3. In some embodiments of the composition of paragraph 1 or 2, the matrix and fermentation solids are at a ratio of at least 6:1, at least 10:1, at least 20:1, at least 50:1, and even at least 100:1, or more on a weight basis.

4. In some embodiments, the composition of any of the previous paragraphs has a water activity of at least 0.35 at 20° C.

5. In some embodiments, the composition of any of the previous paragraphs further has greater than 1%, greater than 3%, and even greater than 5%, and up to 30% water by weight when stored at a relative humidity of 50% and a temperature of 20° C.

6. In some embodiments, the composition of any of the previous paragraphs substantially lacks the protective stabilizer.

7. In some embodiments, the composition of any of the previous paragraphs comprises the protective stabilizer.

8. In some embodiments of the composition of any of the previous paragraphs, the fermentation solids are distributed within the matrix.

9. In some embodiments of the composition of any of the previous paragraphs, the binder is polyvinyl alcohol.

10. In some embodiments of the composition of any of the previous paragraphs, the detackifier is talc.

11. In some embodiments of the composition of any of the previous paragraphs, the protective stabilizer is trehalose or sorbitol.

12. In some embodiments of the composition of any of the previous paragraphs, the fermentation solids comprise microbial structures of bacteria and/or fungi.

13. In some embodiments of the composition of any of the previous paragraphs, the fermentation solids comprise microbial structures of an entomopathogenic fungus.

14. In another aspect, a particle or granule comprising the composition of any of the previous paragraphs is provided.

15. In some embodiments, the particle or granule of paragraph 14, has a unitary structure.

16. In some embodiments, the particle or granule of paragraph 14, has a compound structure.

17. In another aspect, a seed treatment, foliar treatment, in-furrow treatment, animal feed supplement, human probiotic, or personal care product comprising the composition of any of the previous paragraphs is provided.

18. In another aspect, a method for preparing a composition comprising fermentation solids embedded in a matrix to form an evaporated suspension is provided, comprising: (a) combining fermentation solids with a non-hygroscopic matrix at a ratio of 1:1 or higher on a weight basis to form a suspension containing fermentation solids having a water content of a least 50% by weight; and (b) partially drying the suspension containing fermentation solids at a temperature between 0° C. and 50° C. until the resulting evaporated suspension reaches a water activity not lower than 0.35 under ambient conditions.

19. In some embodiments of the method of paragraph 18, the matrix comprises a moisture-regulating binder and a detackifier at a ratio of between 1:5 and 5:1 on a weight basis and not more than 75% protective stabilizer in the matrix.

20. In some embodiments of the method of paragraph 19, the protective stabilizer, binder, and detackifier each have less than 10% water uptake at 50% relative humidity.

21. In some embodiments of the method of paragraph 20, the protective stabilizer, binder, and detackifier each have less than 10% water uptake at 75% relative humidity.

22. In some embodiments of the method of any of paragraphs 18-21, the evaporated suspension has greater than 1%, greater than 3%, and even greater than 5%, and up to 30% water by weight.

23. In some embodiments of the method of any of paragraphs 18-22, the fermentation solids are distributed within the matrix.

24. In some embodiments of the method of any of paragraphs 18-22, the fermentation solids are contacted with the matrix without an intermediate drying step.

25. In some embodiments, the method of any paragraphs 18-24, further comprises the step of making a granule comprising the evaporated suspension.

26. In some embodiments of the method of paragraph 25, the granule has a unitary structure.

27. In some embodiments of the method of paragraph 25, the granule has a compound structure.

28. In some embodiments of the method of any paragraphs 18-27, the evaporated suspension is the evaporated suspension of any of paragraphs 1-13.

These and other aspects and embodiments of present compositions and methods will be apparent from the description.

BRIEF DESCRIPTION OF THE DRAWINGS

FIG. 1 illustrates stable microbial compositions consistent with the description.

DETAILED DESCRIPTION

I. Definitions and Abbreviations

Prior to describing the present strains and methods in detail, the following terms are defined for clarity. Terms not defined should be accorded their ordinary meanings as used in the relevant art.

As used herein, the term "microbes" and "microorganisms" are used interchangeably to refer to microscopic unicellular or multicellular organisms such as, but not limited to, bacteria or fungi.

As used herein, the term "microbial structures" refers to any structure of a microbe or microorganism such as, but not limited to, cells, hyphae, spores, and microsclerotia, or any combination thereof.

As used herein, the term "microsclerotia" refers to small sclerotia, which are fungal structures comprised of compact hyphal aggregates, sometimes melanized, that remain dormant until a favorable opportunity for growth occurs.

As used herein, an "entomopathogenic fungus" is a fungus that is pathogenic to an insect and can thereby disable or kill the insect.

As used herein, "fermentation solids" includes living or dead cells, cell fragments, cell debris, vegetative cells, spores, mycelia, microsclerotia, or any other microbial structures, as well as other soluble and insoluble materials in or derived from a microbial fermentation broth, as harvested or further processed, including any added recovery aids (e.g., precipitants, flocculants, cell-kill reagents, and solubilizers), but excluding any matrix components added for the purpose of stabilizing microbial structures.

As used herein, "viability" refers to the ability to survive and/or live.

As used herein, "stability" refers to the ability to maintain viability through time.

As used herein, "ambient" conditions are defined as 20-30° C. and 30-60% RH. For purposes of defined testing or comparative benchmarking, "ambient conditions" are more specifically stipulated to be 20° C., 1.0 atm and 50% RH.

As used herein, "elevated" humidity is defined as 60-100% RH. For purposes of defined testing or comparative benchmarking, "elevated" humidity is specifically stipulated to be 75% RH.

As used herein, "elevated" temperature is defined as 30-60° C. For purposes of defined testing or comparative benchmarking, "elevated" temperature is specifically stipulated to be 37° C.

As used herein the term "water-soluble" refers to a solute having a solubility in water at 20° C. of at least 1 gram per 100 grams of water.

As used herein, the term "aqueous solution" refers to a solution of a solute containing at least 50% water by weight.

As used herein, the term "water activity (aW)" refers to the partial vapor pressure of water of a composition divided by the standard state partial vapor pressure of water at an indicated time or over the indicated period of time. The standard state is most often defined as the partial vapor pressure of pure water at the same temperature. Unless otherwise specified, water activity is measured at 20° C.

As used herein, the term "relative humidity" ("RH") with respect to a composition refers to the amount of water vapor present in air expressed as a percentage of the amount needed for saturation at the same temperature.

As used herein, the term "water content" or "moisture content" refers to the percentage of water in a composition, expressed gravimetrically as % w/w or wt %.

As used herein the term "water uptake capacity" is defined as the equilibrium water content of a substance stored at a given temperature and humidity. This can be symbolized as $WUC_{(T,RH)}$, where T is the temperature and RH is the relative humidity of storage of the substance. Equilibrium conditions are taken to be sufficiently established when water content measurements change by less than 2% w/w over an interval of at least 24 hours under constant humidity and temperature storage conditions.

As used herein, the term "non-hygroscopic" refers to the property of a substance having a water uptake capacity of at most 10% w/w at 50% RH and 20° C., i.e., $MUC_{(T,RH)}$ ≤10%.

As used herein, the term "hygroscopic" refers to the property of a substance having a water uptake capacity of greater than 10% w/w at 50% RH and 20° C., i.e., $MUC_{(T,RH)}$≥10%

As used herein, the term "moisture-regulating binder," or simply "binder," refers to a water-soluble, but non-hygroscopic, polymer.

As used herein, the term "detackifier" refers to an inorganic or organic compound that reduces the tackiness or adhesiveness of the binder. The detackifier may additional provide additional functionality to the matrix, e.g., as a filler, lubricant, moisture barrier, dispersant, or density modifier.

As used herein, the term "protective stabilizer" refers to a compound that preserves the structure, biological activity and reproductive viability of microbes and microbial structures such as membranes and intracellular proteins to extend the duration of viability when stored at ambient or near-ambient conditions.

As used herein, the term "matrix components," or simply, "matrix," refers to a composition comprising a moisture-regulating binder, a detackifier, and a protective stabilizer, excluding components of fermentation solids.

As used herein, the term "evaporated suspension" refers to a combined suspension of fermentation solids and matrix components from which water has evaporated to the extent that the resulting composition maintains a relatively stable water content of greater than 1% greater than 3%, or greater than 5% w/w, but only up to 30% w/w. An evaporated suspension comprises fermentation solids embedded in a matrix.

As used herein, the term "excipient" refers to conventional formulation components, including, but not limited to, the herein described matrix components.

As used herein, "partially drying" or "partial drying" refers to drawing water from a composition only to the extent that the composition retains more than 1% w/w water, more than 3% w/w water, and preferably more than 5% w/w water.

As used herein, "intermediate drying" refers to drawing water from fermentation solids to the extent that the fermentation solids retain less than 50% w/w water, less than 30% w/w water, or even less than 10% w/w water, prior to combining with matrix.

As used herein, "slow drying" refers to refers to a drying process resulting in no more than 5% w/w water loss per hour.

As used herein, a "seed treatment" is a coating composition, typically comprising a pesticide, microbiocide (i.e. fungicide), growth stimulant, or other chemical or biological material with which seeds are treated, coated or "dressed" prior to planting. A seed treatment may be insecticidal, as in the case of the present compositions and methods.

As used herein, "held" with respect to temperature, simply means to maintain at a specific temperature, with or without agitation.

For ease of reference, elements of the present compositions and methods may be arranged under one or more headings. It is to be noted that the compositions and methods under each of the headings also apply to the compositions and methods under the other headings.

As used herein, the singular articles "a," "an" and "the" encompass the plural referents unless the context clearly dictates otherwise. All references cited herein are hereby incorporated by reference in their entirety. The following abbreviations/acronyms have the following meanings unless otherwise specified:

ATCC American Type Culture Collection
atm atmosphere
aW water activity
CFU colony forming units
° C. degrees Centigrade
G gravity
g gram
g/L grams per liter
g/mol grams per mole
hr or h hour
kg kilogram
LB Luria broth
M molar
mg milligram
mL or ml milliliter
min minute
mm millimeter
micrometer
μg microgram
μL and μl microliter
MUC moisture uptake capacity
MS microsclerotia
PDA potato dextrose agar
psig pounds per square inch, gauge
PVA polyvinyl alcohol
$T_g$ glass transition temperature
TSB tryptic soy broth
rpm revolutions per minute
RH relative humidity
wt % or % w/w weight percent (weight basis)
YE yeast extract
YEG yeast extract glucose
YPD yeast peptone dextrose

II. Compositions and Methods for Stabilization of Microorganisms

A. Introduction

The present compositions and methods solves the problem of stabilizing microbial structures by embedding fermentation solids within a non-hygroscopic matrix that includes a moisture-regulating binder, a detackifier, and a protective stabilizer, and partially drying the matrix/fermentation solids composition such that it retains a moderate amount of water. When stored under ambient temperature and humidity conditions, the resulting evaporated suspension protects microbial structures for a prolonged period of time.

A key feature of the present evaporated suspension is that it retains a moderate water content and water activity throughout processing and during storage under ambient conditions. Previously-described compositions and methods for stabilizing microorganisms rely on drying to very low water activity levels, the use of humidity-controlled packaging, refrigeration, vitrification, or water replacement to "lock in" a glassy state of the embedding matrix. In such previous compositions and methods, it is important to increase the drying temperature and extent of water removal in order to ensure that the final composition has an elevated glass transition temperature ($T_g$). It is common to combine freeze-drying with the use of protective stabilizers to remove most of the water via sublimation at high vacuum and low temperature, before completing the drying process at a higher temperature.

In contrast, the present compositions and methods are based on the surprising observation that microbial structures of various microorganisms can be embedded in a matrix that comprises low-to-moderate amount of free or mobile water at a temperature well above the $T_g$ of the matrix components. While protective stabilizers can enhance the stability of the embedded microbial structure, a significant stabilization is achieved on account of the low hygroscopicity of the selected matrix components. Moreover, the physical stresses induced by freezing, exposure to elevated temperatures, and extreme desiccation at low water content and low water activity, are avoided by the use of an ambient or near-ambient temperature partial-drying process, which is gentler and less damaging to microbial structures.

The amount of matrix, for which constituent components are to be described in further detail, should at least match, and should preferably exceed, the amount of fermentation solids in the evaporated suspension. For example, the ratio of total matrix components to fermentation solids, can be at least 1:1, at least 2:1, at least 4:1, at least 6:1, at least 10:1, at least 20:1, at least 50:1, and even at least 100:1, or more.

B. Moisture-Regulating Binders

The matrix of the present compositions and methods include at least one moisture-regulating binder for the purpose of encapsulating or embedding the fermentation solids in a micro-environment that maintains a water content of about 1-30% w/w water at about 50% RH, or even about 1-30% w/w water at about 75% RH, at a temperature of 20° C. This micro-environment has been found suitable for extending the stability of microbial structures stored under ambient conditions. An additional function of the moisture-regulating binder is to provide a mechanically coherent film suitable for formulation in a granule or other solid application.

The moisture-regulating binder, or simply "binder", is a water-soluble, but non-hygroscopic polymer having a solubility in water of at least 1 gram per 100 mL at 20° C. Exemplary moisture-regulating binders are polyvinyl alcohol (PVA), having a $MUC_{(20,50)}$ of 4% and polyethylene glycol (PEG), having a $MUC_{(20,\ 50)}$ of 1%. A preferred moisture-regulating binder is PVA. Polymers not suitable for use as moisture-regulating binders include polyvinylpyrrolidone (PVP), having a $MUC_{(20,\ 50)}$ of 18% and calcium alginate, having a $MUC_{(20,\ 50)}$ of 20%. Preferred embodiments of the present compositions and methods include the preferred polymers and exclude the aforementioned unsuitable polymers.

C. Detackifiers

The matrix of the present compositions and methods include at least one detackifier for the purpose of reducing the tackiness or adhesiveness of the moisture-regulating binder. Detackifiers are inorganic or organic compounds that neither bind nor repel water. The detackifier may additional provide additional functionality to the matrix, e.g., as a filler, lubricant, moisture barrier, dispersant, or density modifier.

Inorganic detackifiers include minerals such as talc, mica, magnesium silicate, and clays, such as kaolin, montmorillonite, and attapulgite. Organic detackifiers include anionic and ethoxylated surfactants or dispersants. Effective detackifiers tend to be slightly hydrophobic or amphiphilic, with a tendency to associate or form a layer at the surface of a hydrophilic polymeric film. Desiccants that take up or bind significant amounts of water at ambient or elevated humidity, such as zeolites and other molecular sieves, are not suitable as detackifiers. A preferred detackifer is talc. Preferred embodiments of the present compositions and methods include the preferred detackifiers and exclude the aforementioned unsuitable detackifiers.

The detackifier should be present in the matrix at a weight ratio of about 1:5 to 5:1 with respect to the moisture-regulating binder, for example, at least 1:5, at least 1:4, at least 1:3, at least 1:2, at least 1:1, at least 2:1, at least 3:1, at least 4:1, or even at least 5:1.

D. Protective Stabilizers

The matrix of the present compositions and methods may include at least one protective stabilizer for the purpose of preserving the microbial structure, biological activity, and viability of microorganisms, by protecting sub-cellular microorganism components such as cell membranes and intracellular proteins, in order to extend the duration of viability under ambient or near-ambient conditions.

Protective stabilizers include non-reducing monosaccharides and disaccharide sugars, such as trehalose, sucrose, and sorbose; sugar alcohols, such as sorbitol, mannitol, xylitol, erythritol and isomalt; polysaccharides, such as wheat starch or maltodextrin; amino acids such as proline, arginine or glutamic acid, or salts thereof; α-keto-acids such as pyruvate, proteins such as whey protein and casein; intrinsically disordered proteins such as tardigrade protein; and complex natural mixtures of the above components, such as spray-dried milk powder. Preferred protective stabilizers are trehalose and sorbitol.

To maintain the non-hygroscopic property of the moisture-regulating binder and the matrix as a whole, the protective stabilizer should itself be non-hygroscopic, i.e., it should have a moisture uptake capacity of at most 10% at 50% RH and 20° C. Referring to some of the exemplary protective stabilizers, trehalose has a $MUC_{(20, 50)}$ of 1%, sorbitol has a $MUC_{(20, 50)}$ of 5%, mannitol has a $MUC_{(20, 50)}$ of 3%, xylitol has a $MUC_{(20, 50)}$ of 2%, erythritol has a $MUC_{(20, 50)}$ of 2%, isomalt has a $MUC_{(20, 50)}$ of 1%, maltodextrin (DE 17-21) has a $MUC_{(20, 50)}$ of 7%, wheat starch has a $MUC_{(20, 50)}$ of 9%, whey protein has a $MUC_{(20, 50)}$ of 6%, and spray-dried milk powder has a $MUC_{(20, 50)}$ of 1%.

Certain sugars (for example, reducing sugars), polyols, amino acids, and proteins that are otherwise known to stabilize microorganisms in dry, desiccated systems, are hygroscopic and not suitable for use as protective stabilizers in the present compositions and methods. For example, glycerol is a simple polyol that has an $MUC_{(20, 50)}$ of 28%.

Desiccants that take up or bind significant amounts of water at ambient humidity, such as zeolites and other molecular sieves, are also not suitable as stabilizers. Preferred embodiments of the present compositions and methods include the preferred stabilizers and exclude the aforementioned unsuitable stabilizers.

The matrix should comprise between 0% and 75% w/w protective stabilizer, so that at least 25% w/w of the matrix comprises a combination of binder and detackifier. While it is preferred to have protective stabilizer in the matrix, is not essential and is therefore optional. The skilled person can determine, for a given microorganism and storage or use condition, whether the binder and detackifier confer sufficient protection without the stabilizer, and whether the added benefit of stabilizer justifies the cost of including it.

E. Water Content and Water Activity of the Evaporated Suspension

According to the present compositions and methods, the matrix composition is added to fermentation solids and the resulting formulated fermentation solids are dried to form an evaporated suspension that maintains a water activity (aW) above 0.35, above 0.40, above 0.45, or even above 0.50 under ambient conditions. In this context, the term "above" is synonymous with "not lower than." Drying is carried out with static or convective air, maintaining the temperature of the formulated fermentation solids below 50° C., below 45° C., below 40° C., and even below 35° C. Preferably, the drying process is carried out slowly, with less than 5% w/w water removed per hour of drying.

The drying process of the invention can be carried out by any conventional static or convective drying method capable of operating within the above-mentioned temperature limits. Drying can also be carried out simultaneously with granulation or particle formation processes. Suitable drying methods include, but are not limited to: spray-drying; fluidized-bed drying, spray-coating, spray-granulation or agglomeration; drum-granulation, or high-shear granulation.

The final water content of the evaporated suspension should be greater than 1%, greater than 3%, and even greater than 5%, and up to 30% water at about 50% RH, or even at about 75% RH, at a temperature of 20° C.

F. Microorganisms and Microbial Structures

As will be apparent from number of microorganisms exemplified below (i.e., *Bacillus subtilis, Saccharomyces cerevisiae, Trichoderma reesei* and *Metarhizium anisopliae*), the present compositions and methods appear to have broad applicability to microorganisms in different phyla. Gram positive bacilli, yeast, and filamentous fungi are all protected by the present compositions and methods. Any structure of a microbe or microorganism such as, but not limited to, cells, hyphae, spores, and microsclerotia, or any combination thereof, are all protected by the present compositions and methods. There is no reason to anticipate that the present compositions and methods cannot be applied to other microorganisms, or microbial structures, without a more than reasonable expectation of similar results.

G. Further Formulations

The present evaporated suspensions are generally suitable for storage and ready-to use for a variety of applications. Alternatively, the evaporated suspensions can be further formulated into particles or granules for ease of handling and reduced dusting. The granules can be matrix granules, in which the evaporated suspensions are distributed with other components to form a core, or coated granules, in which the evaporated suspensions are coated onto a core.

FIG. 1 illustrates two possible alternative microbial composition structures of the invention, as a uniform, unitary particle comprising an evaporated suspension, and compound structure comprising the evaporated suspension as just one element of the composition, e.g., as a layer over an optional core and with optional coatings. Other structures are possible, wherein the evaporated suspension is just one of several parts or components, including a structure with more than one evaporated suspension.

The other components or the core may include additional active agents, such as fertilizer, enzymes, antibiotics, and the like. The granules may further include one or more additional coating layers, which may further include active ingredients.

H. Applications and Uses

The present evaporated suspensions, or further formulations, thereof, are suitable for use as seed treatments, foliar treatments, in-furrow treatments, animal feed supplements, human probiotics, and/or personal care products. The evaporated suspensions containing microbial structures can be combined with other active ingredients, including nutrients, fertilizer, pesticides, antibiotics, and the like.

Examples

The following examples are intended to illustrate embodiments of the present compositions and methods and should not be construed in any way as limiting.

Example 1. Method for Evaluating the Viability of *Bacillus subtilis, Gluconobacter Cerinus, Saccharomyces Cerevisiae* and *Trichoderma reesei* in Fermentation Solids Serial dilution plating and CFU determination was used to determine the viability of bacteria and fungi in fermentation solids. Fermentation solids were resuspended in 5 mL dilution buffer (TSB broth for *B. subtilis*, PDB broth for *G. cerinus*, YPD broth for *S. cerevisiae*, and YEG for *T reesei*) per 10 mg of fermentation solids. The suspensions were mixed by vortexing, and 10× serial dilutions were made using the same buffer. Portions of the suspension were evenly distributed on the surface of Petri dishes containing agar medium (LB agar for *B. subtilis*, PDA for *G. cerinus*, YPD agar for *S. cerevisiae*, and YEG agar for *T reesei*). The inoculated agar plates were incubated in an incubator (at 37° C. for *B. subtilis* overnight, 25° C. for *G. cerinus* for 2 days, 30° C. for *S. cerevisiae* overnight, and 28° C. for *T reesei* for 2 days). During this time viable microbial structures from the fermentation solids produced colonies on the plate. The colonies were counted and reported as CFU per mg of fermentation solids.

Example 2. Stabilization of Fermentation Solids Containing *T. reesei* Using Excipients The viability and stability of microbial structures of a *T reesei* strain was tested in the presence and in the absence of the formulation excipients polyvinyl alcohol (PVA), talc, and trehalose. A fermentation of *T reesei* was carried out as detailed in U.S. Pat. No. 7,713,725, resulting in a broth with a fermentation solids content of approximately 4%.

The non-filtered, non-concentrated broth of *T reesei* was mixed with the formulation excipients PVA, talc, trehalose, and water in the mass percentage proportions listed in Table 1, and the mixtures were homogenized by hand to fully suspend all insoluble components. To facilitate homogenous mixing, the solid PVA was dissolved in water at a solids concentration of 15 wt % prior to preparation of the suspensions. The suspensions were deposited in 1-mL aliquots on a solid surface, using a micropipette to produce thin films of approximately 200 μm in thickness. These thin films were then dried overnight in a laminar flow hood at room temperature to a water content of between 1% and 10%, thereby embedding the fermentation solids within a matrix comprising the excipients and residual water. About 1 hour after deposition, the water activity of the thin films was above 0.8. After overnight drying, the water activity of the thin films was around 0.53, close to the ambient relative humidity during the drying process. The final compositions of the thin films before and after drying are listed in Tables 1 and 2, respectively.

TABLE 1

Composition of thin film coating mixtures containing
*T. reesei* fermentation solids prior to drying

| | Composition (% w/w) | | | | |
| Formulation | PVA (solid) | Talc | Trehalose | *T. reesei* broth | Water |
|---|---|---|---|---|---|
| Non-formulated | | | | 10.0 | 90.0 |
| Formulated | 8.3 | 16.7 | 16.7 | 10.0 | 48.3 |

TABLE 2

Composition and water activity of thin films containing
*T. reesei* fermentation solids after drying

| | Composition (% w/w) | | | | | |
| | PVA (solid) | Talc | Treha-lose | *T. reesei* fermentation solids | Wa-ter | aW |
| Formulation | | | | | | |
|---|---|---|---|---|---|---|
| Non-formulated | | | | 99.0 | 1.0 | 0.52 |
| Formulated | 18.7 | 37.7 | 37.7 | 0.9 | 5.0 | 0.53 |

These thin films were stored at 24° C. and 51% RH for 0, 3, and 7 days, and viability was measured at the end of each incubation period, as described in Example 1. The viability of the microorganism is expressed as CFU per milligram of *T reesei* fermentation solids in the suspension mixtures. Table 3 summarizes the water content and the viability of each formulation after 0, 3, or 7 days of incubation at 24° C. and 51% RH. The water activity of the films after 3 and 7 days of incubation was within the range of 0.50-0.55, suggesting equilibration of the water activity of the films with the relative humidity in the incubator while maintaining consistent water content. Although the films containing the formulation excipients PVA, talc, and trehalose show increased water content relative to the films containing no excipients, the films containing the formulation excipients also show improved viability over the non-formulated films, with a CFU measurement at least one logarithm higher at each time point.

TABLE 3

Water content and viability of thin films containing *T. reesei* fermentation solids through 7 days of incubation at 24° C. and 51% RH

| | Water content after incubation (% w/w) | | | Viability after incubation (CFU/mg) | | |
| | Days of incubation | | | | | |
| | 0 | 3 | 7 | 0 | 3 | 7 |
|---|---|---|---|---|---|---|
| Non-formulated | 1 | 1 | 1 | $2.0 \times 10^4$ | $1.8 \times 10^3$ | $4.0 \times 10^2$ |
| Formulated | 5 | 4 | 4 | $4.5 \times 10^5$ | $4.4 \times 10^4$ | $4.4 \times 10^3$ |

Example 3. Stabilization of Fermentation Solids Containing *S. cerevisiae* Using Excipients The viability and stability of microbial structures of a *S. cerevisiae* strain in fermentation solids was tested in the presence and in the absence of the formulation excipients PVA, talc, zeolite, trehalose, and sorbitol. A fermentation of *S. cerevisiae* was carried out in medium containing 10 g/L YE, 20 g/L bactopeptone and 20 g/L glucose (side baffled Erlenmeyer 500 mL flask with 100 mL media at 32° C. at 150 rpm), resulting in a fermentation broth, which was then centrifuged to reach a fermentation solids content of approximately 1%.

The non-filtered broth of *S. cerevesiae* was mixed with the formulation excipients PVA, talc, trehalose, zeolite, sorbitol, and water in the mass percentage proportions listed in Table 4, and the mixtures were homogenized by hand to fully suspend all insoluble components. To facilitate homogenous mixing, the solid PVA was dissolved in water at a solids concentration of 15 wt % prior to preparation of the suspensions. The suspensions were deposited in 1-mL aliquots on a solid surface, using a micropipette to produce thin films of approximately 200 μm in thickness. These thin films were then dried overnight in a laminar flow hood at room temperature to a water content of between 0% and 15%, thereby embedding the fermentation solids within a matrix comprising excipients and residual water. About 1 hour after deposition, the water activity of the thin films was above 0.8. After overnight drying, the water activity of the thin films was in the range 0.50-0.60, close to the ambient relative humidity during the drying process. The final compositions and water activities of the thin films after drying are listed in Table 5.

These thin films were stored at 24° C. and 51% RH for 0, 3, 7, 14, and 21 days, and viability was measured at the end of each incubation period as described in Example 1. The viability of the microorganism is expressed as CFU per milligram of *S. cerevisiae* fermentation solids in the suspension mixtures. Table 6 summarizes the water content and the viability of each formulation after 0, 3, 7, 14, and 21 days of incubation at 24° C. and 51% RH. The water content was not measured at the 3- or 21-day time points; however, the water contents measured at other time points suggest that the water contents of the films were relatively stable during incubation. The water activity of the films after 7 and 14 days of incubation was within the range of 0.50-0.55, suggesting equilibration of the water activity of the films with the relative humidity in the incubator while maintaining consistent water content. The viability of *S. cerevesiae* microbial structures in most formulations remains at least one order of magnitude higher than that of the unformulated, dried *S. cerevisiae*, with only the formulation containing zeolite (#SC2) and the formulation lacking a binder or detackifier (#SC7) having a poorer stability than without formulation. Further, while the viability of the unformulated, dried *S. cerevisiae* drops by more than two orders of magnitude between the 0-day and 21-day time points, the viability of *S. cerevisiae* microbial structures in several formulations (#SC1 #SC3, #SC4, #SC6) drops by less than one order of magnitude over the same period, proving a stabilizing effect for the combination of PVA and talc with other excipients. As with the *T reesei* films produced in Example 2, the viability and stability of *S. cerevisiae* microbial structures is not dependent on the moisture content of the films after deposition, suggesting a chemical effect for the stabilization, rather than the ability of the excipients to either retain water or aid drying. Films #SC4 and #SC6, both of which contain 10% water or more after drying and incubation, nevertheless retain high activity over time, suggesting that complete drying of the environment surrounding the organism is not necessary to ensure stability. Films #SC5 and #SC6, which contain increased quantities of trehalose and sorbitol relative to #SC3 and #SC4, do not show significantly increased *S. cerevesiae* microbial structure stability, suggesting there is a limit to the quantity of excipient needed to achieve a stabilizing effect.

TABLE 4

Composition of thin film coating mixtures containing *S. cerevisiae* fermentation solids prior to drying

| | Composition (% w/w) | | | | | | |
| Formulation | PVA (solid) | Talc | Zeolite | Trehalose | Sorbitol | *S. cerevisiae* broth | Water |
|---|---|---|---|---|---|---|---|
| Non-formulated | | | | | | 4.0 | 96.0 |
| #SC1 | 3.0 | 6.0 | | | | 4.2 | 86.8 |
| #SC2 | 3.0 | 6.0 | 6.0 | | | 3.9 | 81.1 |
| #SC3 | 2.9 | 5.9 | | 5.9 | | 3.9 | 81.4 |
| #SC4 | 3.0 | 5.9 | | | 6.0 | 4.0 | 81.1 |
| #SC5 | 3.0 | 5.9 | | 23.8 | | 3.9 | 63.4 |
| #SC6 | 3.0 | 6.0 | | | 24.1 | 1.4 | 65.5 |
| #SC7 | | | | | 6.0 | 3.9 | 91.1 |

TABLE 5

Composition and water activity of thin films containing
*S. cerevisiae* fermentation solids after drying

| | Composition (% w/w) | | | | | | | |
| Formulation | PVA (solid) | Talc | Zeolite | Trehalose | Sorbitol | *S. cerevisiae* fermentation solids | Water | aW |
| --- | --- | --- | --- | --- | --- | --- | --- | --- |
| Non-formulated | | | | | | 100.0 | 0.0 | 0.50 |
| #SC1 | 32.5 | 63.9 | | | | 0.7 | 3.0 | 0.55 |
| #SC2 | 18.6 | 36.0 | 36.0 | | | 0.4 | 9.0 | 0.52 |
| #SC3 | 19.7 | 39.4 | | 39.4 | | 0.4 | 1.0 | 0.56 |
| #SC4 | 18.3 | 36.7 | | | 36.7 | 0.4 | 8.0 | 0.53 |
| #SC5 | 8.6 | 17.3 | | 68.9 | | 0.2 | 5.0 | 0.53 |
| #SC6 | 7.9 | 15.9 | | | 63.0 | 0.2 | 13.0 | 0.59 |
| #SC7 | | | | 83.2 | | 0.8 | 16.0 | 0.57 |

TABLE 6

Water content and viability of thin films containing *S. cerevisiae*
fermentation solids through 21 days of incubation at 24° C. and 51% RH

| | Water content after incubation (% w/w) | | | Viability after incubation (CFU/mg) | | | | |
| | | | | Days of incubation | | | | |
| | 0 | 7 | 14 | 0 | 3 | 7 | 14 | 21 |
| --- | --- | --- | --- | --- | --- | --- | --- | --- |
| Non-formulated | 0 | 0 | 0 | $4.0 \times 10^6$ | $1.6 \times 10^6$ | $5.0 \times 10^4$ | $2.0 \times 10^3$ | $2.0 \times 10^4$ |
| #SC1 | 0 | 0 | 0 | $6.0 \times 10^6$ | $1.4 \times 10^6$ | $3.7 \times 10^6$ | $1.6 \times 10^6$ | $5.8 \times 10^5$ |
| #SC2 | 7 | 8 | 8 | $1.0 \times 10^7$ | $2.0 \times 10^5$ | $1.0 \times 10^4$ | 0 | $1.1 \times 10^3$ |
| #SC3 | 4 | 4 | 3 | $1.8 \times 10^7$ | $1.0 \times 10^7$ | $3.5 \times 10^7$ | $1.0 \times 10^6$ | $2.1 \times 10^6$ |
| #SC4 | 11 | 12 | 12 | $1.4 \times 10^8$ | $2.3 \times 10^7$ | $2.5 \times 10^7$ | $1.4 \times 10^7$ | $2.0 \times 10^7$ |
| #SC5 | 7 | 4 | 3 | $1.5 \times 10^8$ | $8.2 \times 10^6$ | $1.4 \times 10^6$ | $2.0 \times 10^6$ | $1.2 \times 10^6$ |
| #SC6 | 11 | 12 | 12 | $6.6 \times 10^7$ | $2.2 \times 10^7$ | $2.6 \times 10^7$ | $2.0 \times 10^7$ | $3.0 \times 10^7$ |
| #SC7 | 11 | 8 | 8 | $3.0 \times 10^9$ | $9.2 \times 10^6$ | $2.3 \times 10^6$ | $4.4 \times 10^5$ | $6.0 \times 10^5$ |

Example 4. Stabilization of Fermentation Solids Containing *B. subtilis* Using Excipients The viability and stability of microbial structures of a *B. subtilis* strain in fermentation solids was tested in the presence and in the absence of the formulation excipients PVA, talc, zeolite, trehalose, and sorbitol. A fermentation of *B. subtilis* was carried out in tryptic soy broth (TSB) media (side baffled Erlenmeyer 500 mL flask with 100 mL media at 37° C. at 150 rpm), resulting in a fermentation broth, which was then centrifuged to reach a fermentation solids content of approximately 3%. Microscopy revealed that the fermentation broth contained only bacterial cells; no spores were present.

The unfiltered whole broth of *B. subtilis* was mixed with the formulation excipients PVA, talc, trehalose, zeolite, sorbitol, and water in the mass percentage proportions listed in Table 7, and the mixtures were homogenized by hand to fully suspend all insoluble components. To facilitate homogenous mixing, the solid PVA was dissolved in water at a solids concentration of 15 wt % prior to preparation of the suspensions. The suspensions were deposited in 1-mL aliquots on a solid surface, using a micropipette to produce thin films of approximately 200 μm in thickness. These thin films were then dried overnight in a laminar flow hood at room temperature to a water content of between 0% and 20%, thereby embedding the fermentation solids within a matrix comprising excipients and residual water. About 1 hour after deposition, the water activity of the thin films was above 0.8. After overnight drying, the water activity of the thin films was in the range 0.50-0.60, close to the ambient relative humidity during the drying process. The final compositions and water activities of the thin films after drying are listed in Table 8.

These thin films were stored at 24° C. and 51% RH for 0, 3, 7, 14, and 21 days, and viability was measured at the end of each incubation period as described in Example 1. The viability of the microorganism is expressed as CFU per milligram of *B. subtilis* fermentation solids in the suspension mixtures. Table 9 summarizes the water content and the viability of each formulation after 0, 3, 7, 14, and 21 days of incubation at 24° C. and 51% RH. Water content was not measured after 3 or 21 days; however, the water contents measured at other time points suggest that the water contents of the films were relatively stable during incubation. The water activity of the films after 7 and 14 days of incubation was within the range of 0.50-0.55, suggesting equilibration of the water activity of the films with the relative humidity in the incubator while maintaining a consistent water content. The viability of *B. subtilis* in all formulations except for #BS2 and #BS7 remains at least one order of magnitude higher than that of the unformulated, dried *B. subtilis*. These formulations were also among the worst performing for *S. cerevisiae* microbial structures, suggesting that optimal formulation is achieved in the presence of PVA and talc, and in the absence of zeolite. Formulation #BS7 does not contain a binder or a detackifier, and, therefore, produces a thin, papery film that does not effectively suspend the microorganisms within a protective matrix, and would be difficult to formulate for any solid application. Furthermore, while the viability of the unformulated, dried *B. subtilis* drops by more than three orders of magnitude between the 0-day and 21-day time points, the viability of all PVA-talc matrix formulations containing sorbitol or trehalose (#BS3 #BS4, #BS5, #BS6) drops by less than two orders of magnitude over the same period, strongly suggesting that these two excipients act as stabilizers, supported by experimental data across multiple organisms. As with the *T reesei* and *S. cerevisiae* films described in Examples 2 and 3, the stability of *B. subtilis* is not correlated with the moisture content of the films after deposition, suggesting a chemical effect for the stabilization, rather than a simple physical control of the water content of the films by the excipients. In particular, the similar stabilization performance of films that contain less than 5% water after drying (#BS3 and #BS5) and films that contain more than 10% water after drying (#BA4 and #BS6), shows that formulation excipients can be used to stabilize micro-organisms in thin films at either high or low moisture conditions. However, the poor stability of both the non-formulated microorganism (less than 1% water content) and the non-matrix system #BS7 (up to 16% water content) shows that neither a high or low moisture content alone is sufficient to stabilize the microorganism. A correct choice of excipient system is critical to achieving the desired stabilization at various moisture conditions.

TABLE 7

Composition of thin film coating mixtures containing
*B. subtilis* fermentation solids prior to drying

| | Composition (% w/w) | | | | | | |
|---|---|---|---|---|---|---|---|
| Formulation | PVA (solid) | Talc | Zeolite | Trehalose | Sorbitol | *B. subtilis* broth | Water |
| Non-formulated | | | | | | 2.1 | 97.9 |
| #BS1 | 3.0 | 5.9 | | | | 2.1 | 89.0 |
| #BS2 | 3.0 | 5.8 | 5.8 | | | 2.0 | 83.4 |
| #BS3 | 3.0 | 6.0 | | 6.0 | | 2.0 | 83.0 |
| #BS4 | 3.0 | 6.0 | | | 6.0 | 2.0 | 83.0 |
| #BS5 | 3.0 | 6.0 | | 23.9 | | 2.0 | 65.1 |
| #BS6 | 3.0 | 6.0 | | | 23.8 | 2.0 | 67.2 |
| #BS7 | | | | 6.0 | | 2.0 | 92.0 |

TABLE 8

Composition and water activity of thin films containing
*B. subtilis* fermentation solids after drying

| | Composition (% w/w) | | | | | | | |
|---|---|---|---|---|---|---|---|---|
| Formulation | PVA (solid) | Talc | Zeolite | Trehalose | Sorbitol | *B. subtilis* fermentation solids | Water | aW |
| Non-formulated | | | | | | 100.0% | 0.0 | 0.48 |
| #BS1 | 32.6 | 64.2 | | | | 0.2 | 3.0 | 0.54 |
| #BS2 | 18.7 | 36.1 | 36.1 | | | 0.1 | 9.0 | 0.49 |
| #BS3 | 19.8 | 39.5 | | 39.5 | | 0.1 | 1.0 | 0.51 |
| #BS4 | 18.4 | 36.8 | | | 36.8 | 0.1 | 8.0 | 0.55 |
| #BS5 | 8.7 | 17.3 | | 69.0 | | 0.1 | 5.0 | 0.54 |
| #BS6 | 8.7 | 15.9 | | | 63.1 | 0.1 | 13.0 | 0.56 |
| #BS7 | 8.0 | 15.9 | | 83.7 | | 0.3 | 16.0 | 0.57 |

TABLE 9

Water content and viability of thin films containing *B. subtilis* fermentation
solids through 21 days of incubation at 24° C. and 51% RH

| | Water content after incubation (% w/w) | | | Viability after incubation (CFU/mg) | | | | |
|---|---|---|---|---|---|---|---|---|
| | | | | Days of incubation | | | | |
| | 0 | 7 | 14 | 0 | 3 | 7 | 14 | 21 |
| Non-formulated | 0 | 0 | 0 | $1.1 \times 10^8$ | $7.6 \times 10^6$ | $1.6 \times 10^6$ | $1.6 \times 10^6$ | $1.0 \times 10^5$ |
| #BS1 | 3 | 3 | 4 | $3.0 \times 10^8$ | $9.6 \times 10^7$ | $2.8 \times 10^7$ | $2.0 \times 10^7$ | $2.9 \times 10^6$ |
| #BS2 | 9 | 9 | 8 | $5.4 \times 10^7$ | $6.4 \times 10^7$ | $2.1 \times 10^7$ | $5.6 \times 10^6$ | $2.2 \times 10^5$ |
| #BS3 | 1 | 1 | 2 | $1.6 \times 10^9$ | $5.6 \times 10^6$ | $8.1 \times 10^7$ | $3.1 \times 10^7$ | $4.1 \times 10^7$ |
| #BS4 | 8 | 9 | 10 | $1.1 \times 10^9$ | $2.7 \times 10^8$ | $1.1 \times 10^8$ | $4.8 \times 10^6$ | $1.6 \times 10^7$ |
| #BS5 | 5 | 4 | 4 | $1.8 \times 10^8$ | $4.1 \times 10^8$ | $3.0 \times 10^7$ | $1.8 \times 10^7$ | $7.8 \times 10^7$ |
| #BS6 | 13 | 14 | 14 | $5.5 \times 10^8$ | $1.1 \times 10^8$ | $2.1 \times 10^7$ | $5.0 \times 10^6$ | $6.0 \times 10^6$ |
| #BS7 | 16 | 11 | 12 | $2.0 \times 10^7$ | $1.8 \times 10^7$ | $3.8 \times 10^6$ | $3.4 \times 10^5$ | 0 |

Example 5. Method for Evaluating the Viability of *M. anisopliae* Microbial Structures A two-step assay was used to determine the viability of *M. anisopliae* microbial structures (including, but not limited to, microsclerotia, mycelium and spores) in *M. anisopliae* fermentation solids. The first step determines the total number of conidiospores generated from a defined amount of *M. anisopliae* fermentation solids in defined conditions, while the second step determines the total number viable conidiospores from the first step. The additional benefit of the second step is that it can identify fungal contaminants if they can be distinguished based on colony morphology. Therefore, the viability of *M. anisopliae* fermentation solids is expressed through condiospore CFUs generated/mg of *M. anisopliae* fermentation solids.

The two-step assay starts with transferring 10 mg of *M. anisopliae* fermentation solids to a conical tube, and adding 5 mL of dilution buffer. The dilution buffer contains 0.9% sodium chloride and 0.05% Tween 80. The suspensions are mixed by vortexing, and 10-fold serial dilutions are made using the same buffer. Portions of the suspension are evenly distributed on the surface of Petri dishes containing water agar medium. The water agar medium contains 2% agar and is supplemented with 100 µg/mL streptomycin to prevent growth of contaminant organisms. The inoculated water agar plates are incubated in a dark incubator at 28° C. for 8 days. During this time viable microbial structures from the *M. anisopliae* fermentation solids produce colonies on the plate, and aerial conidiospores are generated after the activation of the asexual cycle. Conidiospores are harvested by pouring 10 mL of buffer on the plate surfaces and gently suspending the conidiospores in the dilution buffer using a "hockey stick" spreader. The suspensions are transferred to conical tubes and mixed by vortexing. Serial dilution series are made from the conidiospore suspensions and portions from each dilution of each series are plated on Vogel's minimal medium plates. Vogel's minimal medium is known in the art. The inoculated plates are incubated in a light incubator with a 12 h light/dark cycle for 5 days. The number of colonies are counted and reported as CFU per mg *M. anisopliae* fermentation solids, reflecting the total number of viable conidiospores collected from water agar plates inoculated with a defined amount of *M. anisopliae* fermentation solids.

The two-step assay as described above has a reproducibility of approximately one log, i.e., a factor of 10 CFU per mg *M. anisopliae* fermentation solids, which is adequate for the purposes of assessing storage stability of viable *M. anisopliae* fermentation solids.

Example 6. Stabilization of *M. anisopliae* Fermentation Solids Using Excipients The viability and stability of a *M. anisopliae* strain ATCC 90448 in fermentation solids was tested in the presence and in the absence of the formulation excipients PVA, talc, zeolite, trehalose, and sorbitol. A fermentation of *M. anisopliae* was carried out according to conditions listed in U.S. Patent Pub. No. 2009/0074809, resulting in a fermentation broth with a fermentation solids content of approximately 3%. Microscopy revealed that the fermentation broth contained mycelium, spores, and microsclerotia. The fermentation broth was concentrated via centrifugation and the supernatant was discarded. The fermentation solids content of the broth after concentration was approximately 12%.

After concentration, the microsclerotia content of the fermentation broth increased from $1.1 \times 10^5$ MS/mL to $3.0 \times 10^5$ MS/mL.

The concentrated *M. anisopliae* fermentation solids was mixed with the formulation excipients PVA, talc, trehalose, zeolite, sorbitol, and water in the mass percentage proportions listed in Table 10, and the mixtures were homogenized by hand to fully suspend all insoluble components. To facilitate homogenous mixing, the solid PVA was dissolved in water at a solids concentration of 20 wt % prior to preparation of the suspensions. The suspensions were deposited in 1.0-1.5 mL aliquots on a solid surface, using a micropipette to produce thin films of approximately 200 µm in thickness. These thin films were then dried overnight in a laminar flow hood at room temperature to a water content of between 0% and 10%, thereby embedding the fermentation solids within a matrix comprising excipients and residual water. The water activity properties of the thin films were similar to those described in Examples 2, 3 and 4. About 1 hour after deposition, the water activity of the thin films was above 0.80. After overnight drying, the water activity of the thin films was in the range 0.50-0.60, close to the ambient relative humidity during the drying process. The final compositions of the thin films after drying are listed in Table 11.

The thin films were stored at 24° C. and 51% RH for 0, 3, and 7 days, and viability of microbial structures from *M. anisopliae* fermentation solids was measured at the end of each incubation period as described in Example 5. As in examples 2, 3 and 4, the water activity of the films after incubation was within the range of 0.50-0.55, suggesting equilibration of the water activity of the films with the relative humidity in the incubator while maintaining a consistent water content. The viability of the films is expressed as CFU per milligram of *M. anisopliae* fermentation solids in the suspension mixtures. Table 12 summarizes the water content and the viability of each formulation after 0, 3, and 7 days of incubation at 24° C. and 51% RH. Whereas the non-formulated fermentation solids showed no viability after 3 days of incubation, all formulated fermentation solids show minimal or no loss in viability through the 7-day time point, proving that all excipients tested are successful in stabilizing a microsclerotia-containing *M. anisopliae* fermentation solids concentrate. Among the different formulation excipients tested, the lowest viability was observed for the thin films containing zeolite (#MA2), suggesting that this excipient has the least-positive effect of those tested within a PVA-talc matrix. A similar result for zeolite was observed for thin films of *S. cerevisiae* and *B. subtilis* in Examples 3 and 4. Unlike in the examples of *S. cerevisiae* and *B. subtilis* thin films, trehalose alone (#MA5) is shown to provide a stabilizing effect, absent the PVA-talc matrix; however, stabilizing *M. anisopliae* in a matrix of trehalose alone would present solid formulation challenges, due to the poor adhesion of a trehalose film to any substrate, as well as the poor dispersibility of films or particles comprising fermentation solids and trehalose alone, without the presence of PVA and talc. The varying water contents of the thin films suggests that, as for *S. cerevisiae* and *B. subtilis*, a correct choice of formulation excipients can be selected to stabilize microsclerotia-containing *M. anisopliae* fermentation solids at a variety of moisture conditions.

TABLE 10

Composition of thin film coating mixtures containing
*M. anisopliae* fermentation solids prior to drying

| | Composition (% w/w) | | | | | | |
|---|---|---|---|---|---|---|---|
| Formulation | PVA (solid) | Talc | Zeolite | Trehalose | Sorbitol | *M. anisopliae* fermentation concentrate | Water |
| Non-formulated | | | | | | 3.0 | 97.0 |
| #MA1 | 3.4 | 6.6 | | | | 2.0 | 88.0 |
| #MA2 | 3.3 | 6.6 | 6.6 | | | 2.0 | 81.5 |
| #MA3 | 3.3 | 6.6 | | 6.6 | | 2.1 | 81.4 |
| #MA4 | 3.3 | 6.7 | | | 6.7 | 2.0 | 81.3 |
| #MA5 | | | | 10.0 | | 3.0 | 87.0 |

TABLE 11

Composition of thin films containing *M. anisopliae* fermentation solids after drying

| | Composition (% w/w) | | | | | | |
|---|---|---|---|---|---|---|---|
| Formulation | PVA (solid) | Talc | Zeolite | Trehalose | Sorbitol | *M. anisopliae* fermentation solids | Water |
| Non-formulated | | | | | | 100.0 | 0.0 |
| #MA1 | 32.2 | 62.5 | | | | 2.3 | 3.0 |
| #MA2 | 18.3 | 36.7 | 36.7 | | | 1.3 | 7.0 |
| #MA3 | 19.3 | 38.6 | | 38.6 | | 1.5 | 2.0 |
| #MA4 | 18.1 | 36.8 | | | 36.8 | 1.3 | 7.0 |
| #MA5 | | | | 95.6 | | 3.4 | 1.0 |

TABLE 12

Water content and viability of thin films containing
*M. anisopliae* fermentation solids through
7 days of incubation at 24° C. and 51% RH

| | Water content after incubation (% w/w) | | | Viability after incubation (CFU/mg) | | |
|---|---|---|---|---|---|---|
| | Days of incubation | | | | | |
| | 0 | 3 | 7 | 0 | 3 | 7 |
| Non-formulated | 0 | 0 | 0 | $1.9 \times 10^7$ | 0 | 0 |
| #MA1 | 3 | 3 | 3 | $1.2 \times 10^7$ | $6.3 \times 10^6$ | $2.7 \times 10^7$ |
| #MA2 | 7 | 7 | 6 | $1.1 \times 10^7$ | $5.6 \times 10^6$ | $1.0 \times 10^7$ |
| #MA3 | 2 | 1 | 0 | $1.0 \times 10^8$ | $3.1 \times 10^7$ | $1.5 \times 10^9$ |
| #MA4 | 7 | 7 | 7 | $6.6 \times 10^7$ | $6.1 \times 10^7$ | $5.9 \times 10^9$ |
| #MA5 | 1 | 0 | 0 | $9.4 \times 10^7$ | $7.4 \times 10^7$ | $1.5 \times 10^9$ |

Example 7. Effect of Recovery and Concentration
Conditions on the Stability of *M. anisopliae*
Fermentation Solids The viability and stability of *M. anisopliae* strain ATCC 90448 fermentation solids was tested in the presence and in the absence of the formulation excipients PVA, talc, zeolite, trehalose, and sorbitol. A fermentation of *M. anisopliae* was carried out according to conditions listed in U.S. Patent Pub. No. 2009/0074809, resulting in a fermentation broth with a solids content of approximately 7%. Microscopy revealed that the fermentation broth contained mycelium, spores, and microsclerotia.

The fermentation broth was diluted with approximately one-part water per part broth (by weight), sieved to remove large particulates (greater than 1 mm) and concentrated via centrifugation, after which the supernatant was discarded. The total fermentation solids content of the cell paste after centrifugation was approximately 10%; this is referred to as "unwashed cell paste." The unwashed cell paste was then resuspended in approximately five-parts water per part cell paste (by weight), concentrated by centrifugation and the supernatant again discarded. This is referred to as "washed cell paste" and had a fermentation solids content of approximately 7%. The washed cell paste was then spread into a thin layer on a weigh boat and allowed to dry for approximately two days at ambient conditions. The fermentation solids content of the dried material was approximately 35%. After each step of centrifuging and discarding the supernatant, the fermentation solids became more concentrated in terms of microorganism solids.

The four concentrated preparations of *M. anisopliae* fermentation solids were mixed with the formulation excipients PVA, talc, trehalose, and water in the mass percentage proportions listed in Table 13, and the mixtures were homogenized by hand to fully suspend all insoluble components. To facilitate homogenous mixing, the solid PVA was dissolved in water at a solids concentration of 20 wt % prior to preparation of the suspensions. Each sample contained a trehalose: *M. anisopliae* fermentation solids ratio of approximately 3.33:1. The suspensions were deposited in 1 to 1.5 mL aliquots on a solid surface, using a micropipette to produce thin films of approximately 200 μm in thickness. These thin films were then dried overnight in a laminar flow hood at room temperature to a water content of between 0% and 10%, thereby embedding the fermentation solids within a matrix comprising excipients and residual water. The water contents of the films were similar to those described in previous experiments, with the non-formulated films containing about 1% or less water, and the films using the PVA-talc-trehalose matrix formulation containing about 4-5% water. The water activity properties of the thin films were similar to those described in Examples 2, 3 and 4. About 1 hour after deposition, the water activity of the thin films was above 0.80. After overnight drying, the water activity of the thin films was in the range 0.45-0.60, close to the ambient relative humidity during the drying process. The final compositions of the thin films after drying are listed in Table 14.

The thin films were stored at 24° C. and 51% RH for 0, 3, 7, 14, and 21 days, and viability was measured at the end of each incubation period as described in Example 5. As in examples 2, 3 and 4, the water activity of the films after incubation was within the range of 0.5-0.55, suggesting equilibration of the water activity of the films with the relative humidity in the incubator while maintaining a consistent water content. The viability of the MS is expressed as CFU per milligram of *M. anisopliae* fermentation solids in the suspension mixtures. Table 15 summarizes the viability of each formulation after 0, 3, 7, 14, and 21 days of incubation at 24° C. and 51% RH. Without the formulation excipients, no sample showed viability after 7 days of incubation, while all samples containing the formulation excipients show minimal or no loss in viability through the 21-day time point, proving that the PVA-talc-trehalose matrix is successful in stabilizing microsclerotia in *M. anisopliae* fermentation solids, even after a variety of different processing methods. Among the different processing methods tested, the unformulated dried fermentation solids had the lowest stability, showing no viability after three days of incubation. This suggests that less processing of the *M. anisopliae* fermentation solids concentrate prior to formulation, and in particular less drying prior to rehydration, provides a superior formulation result.

TABLE 14

Composition of thin films containing *M. anisopliae* fermentation solids, after drying

| | Composition (% w/w) | | | | |
| Formulation | PVA | Talc | Trehalose | *M. anisopliae* fermentation solids | Water |
|---|---|---|---|---|---|
| Broth, non-fomulated | 0.0 | 0.0 | 0.0 | 100.0 | 0.0 |
| Broth, formulated | 17.1 | 34.2 | 34.2 | 10.4 | 4.0 |
| Unwashed, non-formulated | 0.0 | 0.0 | 0.0 | 100.0 | 0.0 |
| Unwashed, formulated | 16.8 | 34.0 | 34.0 | 10.1 | 5.0 |
| Washed, non-formulated | 0.0 | 0.0 | 0.0 | 100.0 | 0.0 |
| Washed, formulated | 16.9 | 33.9 | 33.9 | 10.3 | 5.0 |
| Dried, non-formulated | 0.0 | 0.0 | 0.0 | 100.0 | 0.0 |
| Dried, Formulated | 17.0 | 34.4 | 34.4 | 10.2 | 4.0 |

TABLE 13

Composition of thin film coating mixtures containing *M. anisopliae* fermentation solids, prior to drying
Composition (% w/w)

| Formulation | PVA | Talc | Trehalose | *M. anisopliae* fermentation concentrate | Water | Fermentation solids content of *M. anisopliae* concentrate |
|---|---|---|---|---|---|---|
| Broth, non-fomulated | | | | 45.2 | 54.8 | 6.7 |
| Broth, formulated | 5.0 | 10.0 | 10.0 | 45.3 | 29.7 | 6.7 |
| Unwashed, non-formulated | | | | 29.4 | 70.6 | 10.1 |
| Unwashed, formulated | 5.0 | 10.1 | 10.1 | 29.8 | 45.0 | 10.1 |
| Washed, non-formulated | | | | 41.7 | 58.3 | 7.2 |
| Washed, formulated | 5.0 | 10.0 | 10.0 | 42.0 | 33.0 | 7.2 |
| Dried, non-formulated | | | | 8.7 | 91.3 | 35.0 |
| Dried, Formulated | 5.0 | 10.1 | 10.1 | 8.6 | 66.2 | 35.0 |

TABLE 15

Viability of thin films containing *M. anisopliae* fermentation
solids through 7 days of incubation at 24° C. and 51% RH

| | Viability after incubation (CFU/mg) Days of incubation | | | | |
|---|---|---|---|---|---|
| | 0 | 3 | 7 | 14 | 21 |
| Broth, non-fomulated | $9.3 \times 10^4$ | $6.6 \times 10^4$ | 0 | 0 | 0 |
| Broth, formulated | $1.6 \times 10^6$ | $3.3 \times 10^6$ | $1.1 \times 10^6$ | $4.7 \times 10^5$ | $1.0 \times 10^6$ |
| Unwashed, non-formulated | $5.6 \times 10^4$ | $5.8 \times 10^4$ | 0 | 0 | 0 |
| Unwashed, formulated | $2.6 \times 10^6$ | $7.8 \times 10^5$ | $1.4 \times 10^6$ | $4.0 \times 10^5$ | $7.5 \times 10^5$ |
| Washed, non-formulated | $2.0 \times 10^5$ | $1.1 \times 10^5$ | 0 | 0 | 0 |
| Washed, formulated | $2.8 \times 10^6$ | $2.4 \times 10^6$ | $4.2 \times 10^5$ | $3.6 \times 10^5$ | $5.9 \times 10^5$ |
| Dried, non-formulated | $9.0 \times 10^4$ | 0 | 0 | 0 | 0 |
| Dried, Formulated | $1.1 \times 10^6$ | $1.3 \times 10^6$ | $5.3 \times 10^5$ | $3.8 \times 10^5$ | $4.4 \times 10^5$ |

Example 8. Stabilization of *M. anisopliae* Fermentation Solids in a Granule Granules containing *M. anisopliae* strain ATCC 90448 fermentation solids were produced using the formulation excipients PVA, talc, and trehalose. The concentrated fermentation broth described in Example 6, with a fermentation solids-content of approximately 12% and a microsclerotia content of $3.0 \times 10^5$ MS/mL, was used to prepare the macrocapsule. Prior to formulation, the concentrated fermentation broth was passed through an 800-μm sieve. Microscopy revealed that the fermentation broth contained mycelium, spores, and microsclerotia.

Granules containing *M. anisopliae* fermentation solids were produced using a Vector VFC-LAB1 spray coater. The granules were produced by charging the spray-coater with 930 g of salt cores, approximately 200-250 μm in size. The salt cores were subsequently coated with an active layer containing *M. anisopliae* fermentation solids and excipients, followed by a sealing layer of sodium sulfate. The final quantity of granules produced was 1680 g. The spray conditions used to produce the *M. anisopliae* fermentation solids-containing granules are detailed in Table 16. The resulting granules contained approximately 47% sodium sulfate core, 8% *M. anisopliae* fermentation solids, 12% talc, 8% trehalose, 4% PVA, and 21% sodium sulfate sealing layer. The final water content of the granule was about 1%, and if all of the water were assumed to be contained in the evaporated suspension (excluding the core and sealing layer), the water content of this layer alone would be about 4%, commensurate with previous examples of thin films containing PVA, talc, trehalose, and a microorganism.

TABLE 16

Spray conditions for production of a fluid-bed-coated
granule containing *M. anisopliae* fermentation solids

| | Evaporated suspension | Sealing layer |
|---|---|---|
| | Spray mixtures | |
| *M. anisopliae* concentrate (12% fermentation solids), g | 1000 | |

TABLE 16-continued

Spray conditions for production of a fluid-bed-coated
granule containing *M. anisopliae* fermentation solids

| | Evaporated suspension | Sealing layer |
|---|---|---|
| Talc, g | 180 | |
| Trehalose, g | 120 | |
| Mowiol 5-88 PVA, 15% solution, g | 400 | |
| Sodium sulfate, g | | 333 |
| Water, g | 700 | 1333 |
| | Spray parameters | |
| Initial sodium sulfate core charge, g | 930 | — |
| Spray mixture feed rate, g/min | 12 | 20 |
| Atomization air pressure, psig | 30 | 30 |
| Bed temperature, ° C. | 35 | 35 |
| Spray yield, % | 93 | 90 |

The *M. anisopliae* fermentation solids-containing granules were stored at 24° C. and 51% RH for 0, 3, 7, and 14 days, and viability was measured at the end of each incubation period as described in Example 5. An aliquot of the PVA-talc-trehalose-*M. anisopliae* fermentation solids spray mixture used for coating the evaporated suspension layer was also taken and incubated at the same conditions, as was an aliquot of the unformulated *M. anisopliae* fermentation solids. The viability of each aliquot after incubation is expressed as CFU per milligram of *M. anisopliae* fermentation solids in the granule or spray mixture. Table 17 summarizes the viability of each formulation after 0, 3, 7, and 14 days of incubation at 24° C. and 51% RH. As in previous examples, the PVA-talc-trehalose excipient matrix clearly shows a stabilizing effect, with the unformulated fermentation solids showing a loss of viability after 7 days, while the formulated fermentation solids show viability to at least 14 days. The *M. anisopliae* fermentation solids encapsulated in the granule exhibit stability similar to those contained in the PVA-talc-trehalose spray mixture alone. Thus, despite the additional stresses of mixing, spraying, and holding at elevated temperature in a fluidized bed, the stabilization in the granules is approximately equal to the stabilization achieved using the excipients alone. The stabilization showed for various microorganisms in model thin-film systems in previous examples can therefore also be achieved in a more practical, easier-to-handle granular form.

TABLE 17

Viability of granules containing *M. anisopliae* fermentation
solids through 14 days of incubation at 24° C. and 51% RH

| | Viability of *M. anisopliae* solids after incubation (CFU/mg) Days of incubation | | | |
| | 0 | 3 | 7 | 14 |
| --- | --- | --- | --- | --- |
| Unformulated | $1.2 \times 10^8$ | $2.2 \times 10^5$ | 0 | 0 |
| Spray mixture | $8.4 \times 10^7$ | $1.4 \times 10^9$ | $1.4 \times 10^7$ | $2.3 \times 10^4$ |
| Finished granule | $1.3 \times 10^8$ | $3.1 \times 10^9$ | $7.2 \times 10^6$ | $1.4 \times 10^5$ |

Example 9. Stabilization of *Gluconobacter cerinus* Fermentation Solids in a Granule Matrix granules containing *G. cerinus* fermentation solids were produced using the formulation excipients PVA, talc, and trehalose, and via continuous spray-granulation on a Glatt ProCell LabSystem 5 (Glatt GmbH, Binzen, Germany) spray-granulation apparatus. In contrast to the coated granules with a compound structure described in Example 8 and illustrated as Composition Type 2 in FIG. 1, the *G. cerinus* matrix granules represent a unitary structure, illustrated as Composition Type 1 in FIG. 1.

A fermentation of *G. cerinus* was produced in 15 L SIP/CIP fermentor. The fermentation media consisted of an aqueous suspension of yeast extract (5-10 g/kg), soymeal (5-10 g/kg), magnesium sulfate heptahydrate (1-3 g/kg), potassium phosphate monobasic (0.5-2 g/kg), ammonium sulfate (0.5-1.5 g/kg), a trace elements solution similar to the Modified Trace Metals Solution from Teknova (2 mL/kg) along with antifoam (1 g/kg). Calcium chloride dihydate (2-4 g/L) and glucose (50 g/L) was added as following sterilization. The pH was maintained at 5.5 using aqueous ammonia, and the temperature maintained at 30° C. The feed, consisting of 60% w/w glucose solution, was fed starting at 30 hr and continued until the end of the run (72 hr) at a rate of 0.95 g/min.

The fermentation broth was subsequently concentrated by centrifugation in a Sorvall RC 12BP centrifuge equipped with six, 2,000 ml swinging containers. The centrifuge containers, holding a total of 8,000 grams of fermentation broth, were spun at 4,000×G for 25 minutes at an operating temperature of 10° C. 6,400 grams of supernatant was decanted, and the sediment resuspended with the remaining supernatant, resulting in a 5× concentrated suspension of fermentation solids compared to the end-of-fermentation broth. This produced a concentrated fermentation broth, with a fermentation solids-content of approximately 15.5% and a viability of $2.8 \times 10^8$ CFU/mL, which was used to prepare the granules.

Granules containing *G. cerinus* fermentation solids were produced using a Glatt ProCell LabSystem 5 spray-granulation apparatus. The granules were produced by first charging the ProCell equipment with 450 g of inert granules ranging between approximately 400-600 μm in size. The inert granules consisted of PVA, talc, trehalose, and lysed fermentation solids. The bed of inert granules was fluidized, and into this fluidized bed, an active spray mixture consisting of PVA, talc, trehalose, and *G. cerinus* was sprayed, while granules from the bed were simultaneously removed from the system via recirculation through a passage containing a zig-zag sifter. The final quantity of active granules produced after 5 hours of spraying was 1200 g. As the active mixture was sprayed continuously and granules from the bed were removed continuously, the bed of inert granules was gradually replaced with a bed of active granules containing the *G. cerinus* fermentation solids. Comparison of the viability of granules taken at various times during the continuous granulation process suggests that the bed had recirculated sufficiently to reach a steady-state viability after about 90 minutes, with granules removed from the bed after this amount of time showing viability equivalent to those removed at the end of the run. The spray conditions used to produce the *G. cerinus* fermentation solids-containing granules are detailed in Table 18. The resulting granules contained approximately 6% w/w *G. cerinus* fermentation solids, 52% w/w talc, 12% w/w trehalose, and 26% w/w PVA, with a water content of 4% w/w. The water activity of the granules immediately after granulation was about 0.4, and gradually increased to about 0.45 after 7 days of storage at 45% relative humidity.

TABLE 18

Spray conditions for production of a spray-granulated
granule containing *G. cerinus* fermentation solids

| | Evaporated suspension |
| --- | --- |
| Spray mixtures | |
| *G. cerinus* concentrate (15.5% fermentation solids), g | 1130 |
| Talc, g | 1200 |
| Trehalose, g | 750 |
| Mowiol 5-88 PVA, 15% solution, g | 4000 |
| Water, g | 2450 |
| Spray parameters | |
| Spray mixture feed rate, g/min | 18-22 |
| Atomization air pressure, bar | 4.3 |
| Bed temperature, ° C. | 45-55 |
| Spray yield, % | 81 |
| Granule parameters | |
| Water content, % | 4 |
| Water activity at production | 0.40 |
| Water activity after 7 days incubation at 45% RH | 0.45 |

The *G. cerinus* fermentation solids-containing granules were stored at 22° C. and 45% RH for 0, 7, 33, and 104 days, and viability of an aliquot of the samples was measured at the end of each incubation period as described in Example 1. Table 19 summarizes the viability of the granules after 0, 7, 33, and 104 days of incubation at 22° C. and 45% RH. The concentrate, granules, and spray mixture all show no loss of viability after 104 days of storage at this temperature. Furthermore, the water content of the stored granules did not change appreciably from the original 4% w/w. Thus, despite the additional stresses of mixing, spraying, and holding at elevated temperature in a fluidized bed, the stabilization in the granules is approximately equal to the stability of liquid preparations of the microbe. Furthermore, the viability of the microbes in the granules after 0 days per unit fermentation solids was approximately equivalent to that of the formulated and unformulated liquids, suggesting that no viability was lost in the spray-granulation process. The stabilization showed for various microorganisms in model thin-film systems in previous examples can therefore also be achieved in a more practical, easier-to-handle granular form that is readily dispersible in water.

TABLE 19

Viability of granules containing *G. cerinus* fermentation
solids through 104 days of incubation at 22° C. and 45% RH

| | Viability of *G. cerinus* samples after incubation (CFU/mg of fermentation dry solids in sample) Days of incubation | | | |
|---|---|---|---|---|
| | 0 | 7 | 33 | 104 |
| Finished granule | $6.0 \times 10^8$ | $8.2 \times 10^8$ | $7.6 \times 10^8$ | $9.8 \times 10^8$ |

What is claimed is:

1. A microbial composition for stabilizing microorganisms for extended storage under ambient conditions without refrigeration, humidity or special packaging, said composition comprising fermentation solids embedded in a matrix forming an evaporated suspension, characterized by the features of having: a non-hygroscopic matrix and fermentation solids at a ratio of at least 1:1 by weight; wherein the matrix comprises a moisture-regulating binder and a detackifier at a ratio of between 1:5 and 5:1 by weight and, optionally, not more than 75% by weight protective stabilizer; wherein the evaporated suspension has a water content of at least 1% and at most 30% water by weight when stored at a relative humidity of 50% and a temperature of 20° C., and wherein the fermentation solids are distributed within the matrix.

2. The composition of claim 1, wherein the binder, detackifier, and optional protective stabilizer each have less than 10% water uptake at 50%, and optionally 75%, relative humidity.

3. The composition of claim 1, wherein the matrix and fermentation solids are at a ratio of at least 6:1 on a weight basis.

4. The composition of claim 1, having a water activity of at least 0.35 at 20° C.

5. The composition of claim 1, further having greater than 1% water by weight when stored at a relative humidity of 50% and a temperature of 20° C.

6. The composition of claim 1, lacking the protective stabilizer.

7. The composition of claim 1, wherein the binder is polyvinyl alcohol.

8. The composition of claim 1, wherein the detackifier is talc.

9. The composition of claim 1, wherein the protective stabilizer is trehalose or sorbitol.

10. The composition of claim 1, wherein the fermentation solids comprise microbial structures of bacteria and/or fungi.

11. The composition of claim 1, wherein the fermentation solids comprise microbial structures of an entomopathogenic fungus.

12. A particle or granule comprising the composition of claim 1.

13. The particle or granule of claim 12, having a unitary structure.

14. The particle or granule of claim 12, having a compound structure.

15. A seed treatment, foliar treatment, in-furrow treatment, animal feed supplement, human probiotic, or personal care product comprising the composition of claim 1.

16. A method for preparing a composition comprising fermentation solids embedded in a matrix to form an evaporated suspension, comprising:
(a) combining fermentation solids with a non-hygroscopic matrix at a ratio of 1:1 or higher on a weight basis to form a suspension containing fermentation solids having a water content of a least 50% by weight; and
(b) partially drying the suspension containing fermentation solids at a temperature between 0° C. and 50° C. until the resulting evaporated suspension reaches a water activity not lower than 0.35 under ambient conditions.

17. The method of claim 16, wherein the matrix comprises a moisture-regulating binder and a detackifier at a ratio of between 1:5 and 5:1 on a weight basis and not more than 75% protective stabilizer in the matrix.

18. The method of claim 17, wherein the protective stabilizer, binder, and detackifier each have less than 10% water uptake at 50% relative humidity.

19. The method of claim 18, wherein the protective stabilizer, binder, and detackifier each have less than 10% water uptake at 75% relative humidity.

20. The method of claim 16, wherein the evaporated suspension has greater than 1%, greater than 3%, and even greater than 5%, and up to 30% water by weight.

21. The method of claim 16, wherein the fermentation solids are distributed within the matrix.

22. The method of claim 16, wherein the fermentation solids are contacted with the matrix without an intermediate drying step.

23. The method of claim 16, further comprising the step of making a granule comprising the evaporated suspension.

24. The method of claim 23, wherein the granule has a unitary structure.

25. The method of claim 23, wherein the granule has a compound structure.

26. The method of claim 16, wherein the evaporated suspension is characterized by the features of having: a non-hygroscopic matrix and fermentation solids at a ratio of at least 1:1 by weight; wherein the matrix comprises a moisture-regulating binder and a detackifier at a ratio of between 1:5 and 5:1 by weight and, optionally, not more than 75% by weight protective stabilizer; wherein the evaporated suspension has a water content of at least 1% and at most 30% water by weight when stored at a relative humidity of 50% and a temperature of 20° C.

27. The composition of claim 1, wherein the matrix and fermentation solids are at a ratio of at least 10:1 on a weight basis.

28. The composition of claim 1, wherein the matrix and fermentation solids are at a ratio of at least 20:1 on a weight basis.

29. The composition of claim 1, wherein the matrix and fermentation solids are at a ratio of at least 50:1 on a weight basis.

30. The composition of claim 1, wherein the matrix and fermentation solids are at a ratio of at least 100:1 or more on a weight basis.

* * * * *